(12) United States Patent
Eymery et al.

(10) Patent No.: US 12,311,375 B2
(45) Date of Patent: May 27, 2025

(54) NEST FOR THE PACKAGING OF PLUNGER STOPPERS WITH CLIPS ENSURING A RELIABLE ALIGNMENT OF SEVERAL NESTS IN A TUB

(71) Applicant: Becton Dickinson France, Le Pont-de-Claix (FR)

(72) Inventors: Anaïs Eymery, Saint-Georges-de-Commiers (FR); Camille Maury, Grenoble (FR); Clémentine Le Loc'h, Meylan (FR); Ferdinand Lavigne, Seyssinet-Pariset (FR); Gildas Esnault, Grenoble (FR); Laurent Jacquier, Saint Cassien (FR)

(73) Assignee: Becton Dickinson France, Le Pont de Claix (FR)

( * ) Notice: Subject to any disclaimer, the term of this patent is extended or adjusted under 35 U.S.C. 154(b) by 0 days.

(21) Appl. No.: 18/274,055

(22) PCT Filed: Jan. 26, 2022

(86) PCT No.: PCT/EP2022/051752
§ 371 (c)(1),
(2) Date: Jul. 25, 2023

(87) PCT Pub. No.: WO2022/162002
PCT Pub. Date: Aug. 4, 2022

(65) Prior Publication Data
US 2025/0083152 A1    Mar. 13, 2025

(30) Foreign Application Priority Data
Jan. 26, 2021 (EP) .................................... 21305100

(51) Int. Cl.
*B01L 9/00* (2006.01)
*B65D 25/10* (2006.01)

(52) U.S. Cl.
CPC ........... *B01L 9/54* (2013.01); *B01L 2200/025* (2013.01); *B01L 2300/0809* (2013.01)

(58) Field of Classification Search
CPC . A61M 5/00; A61M 5/008; B01L 9/54; B01L 2200/025; B01L 2300/0809; B65D 25/10; B65D 25/108
(Continued)

(56) References Cited

U.S. PATENT DOCUMENTS

| | | |
|---|---|---|
| 2,650,052 A | 8/1953 | Bintz |
| 8,453,838 B2 | 6/2013 | Hill |

(Continued)

FOREIGN PATENT DOCUMENTS

| | | |
|---|---|---|
| EP | 3454064 A1 | 3/2019 |
| WO | 2012143533 A1 | 10/2012 |

*Primary Examiner* — Bryon P Gehman
(74) *Attorney, Agent, or Firm* — The Webb Law Firm (57) ABSTRACT

A nest and tub arrangement for the storage of medical device components including a tub and at least one nest. The tub includes four side surfaces and a plurality of guide ribs extending vertically along the side surfaces, wherein the plurality of guide ribs are inwardly directed and include a friction surface extending vertically thereon. The at least one nest includes a top surface, a bottom surface, a plurality of receptacles for the storage of a plurality of medical device components therein, and a plurality of deflectable clips positioned on side surfaces of the at least one nest. A position of each of the plurality of deflectable clips of the at least one nest corresponds to a position of a respective one of the plurality of guide ribs of the tub, and a portion of each of the plurality of deflectable clips is configured to contact a corresponding friction surface of a respective one of the plurality of guide ribs so as to laterally deflect each of the plurality of deflectable clips inward to align and secure the at least one nest within the tub.

15 Claims, 7 Drawing Sheets

(58) Field of Classification Search
USPC .......................................................... 206/366
See application file for complete search history.

(56) References Cited

U.S. PATENT DOCUMENTS

| | | | |
|---|---|---|---|
| 9,433,944 | B2 | 9/2016 | Blumentritt et al. |
| 11,103,872 | B2 | 8/2021 | Belz et al. |
| 12,098,018 | B2 * | 9/2024 | Nau ..................... B65D 25/108 |
| 2014/0190861 | A1 | 7/2014 | Carrel et al. |
| 2019/0299217 | A1 | 10/2019 | Motadel et al. |

* cited by examiner

NEST FOR THE PACKAGING OF PLUNGER STOPPERS WITH CLIPS ENSURING A RELIABLE ALIGNMENT OF SEVERAL NESTS IN A TUB

CROSS-REFERENCE TO RELATED APPLICATIONS

This application is the United States national phase of International Application No. PCT/EP2022/051752 filed Jan. 26, 2022, and claims priority to European priority application EP 21305100.6, entitled "A Nest for the Packaging of Plunger Stoppers with Clips Ensuring a Reliable Alignment of Several Nests in a Tub", filed Jan. 26, 2021, the entire disclosures of which are hereby incorporated by reference in their entirety.

BACKGROUND

Field of the Disclosure

The present disclosure relates generally to nest and tub arrangements for the packaging of plunger stoppers used in medical devices such as, e.g., syringes. More particularly, the present disclosure relates to a nest and tub arrangement utilizing at least one nest for the packaging of plunger stoppers, each nest having a plurality of deflectable clips to ensure reliable alignment of a plurality of stacked nests within a tub.

Description of the Related Art

As is known in the art, transfer or storage devices for delivery or storage of a medicament, drug, or vaccine (such as, e.g., syringes) utilize a plunger stopper in contact with an inside surface of a generally tubular syringe barrel in order to draw a substance into (or expel a substance from) the device by way of a plunger rod.

Currently, many such devices are filled and assembled using automated filling machines. Not only do such machines improve productivity and accuracy, but they also provide for a substantially sterile and aseptic filling environment. The various components of the devices (e.g., plunger stoppers, syringe barrels, etc.) are separately provided within the filling machines to enable at least some level of automated assembly.

Typically, a plurality of plunger stoppers are provided in bags or in nests (which are also provided in bags) to be accessed by the filling machine during assembly. Conversely, the syringe barrels are generally packaged in nests having numerous "chimneys" formed therein to hold the barrels, with each nest configured to be held at least partially within a tub when introduced into the filling machine.

While the current nests for syringe barrels are specifically designed for use with tubs, the current nests designed for holding plunger stoppers are not configured for use with a specific tub profile, nor do they fit securely within the tubs used for syringe barrels. In some automated filling machines, the lack of a tub for holding the nests of plunger stoppers does not present an issue. However, in other, more recently-designed filling equipment (such as, e.g., the Vanrx SA25 robotic aseptic filling workcell from Vanrx Pharmasystems Inc.), only components packaged in both nests and tubs are capable of being handled. Furthermore, as noted above, currently-available nests for plunger stoppers are not designed to be held within existing tub designs. Thus, if one were to attempt to utilize existing nests and tubs together in relation to plunger stoppers, the combination may result in unreliable positioning and unwanted movement of the nests within the tub, which would be problematic for the robotic handling of the nests within the filling equipment. Documents US2019299217A1, U.S. Pat. No. 9,433,944B2, EP3454064A1 and WO2012143533A1 relate to packaging for containers.

SUMMARY

In view of the foregoing, there exists a need for a nest designed specifically for plunger stoppers, as well as a tub designed specifically to accommodate a plurality of such nests. Additionally, there exists a need for both a nest and tub configured to ensure reliable alignment of a plurality of nests within each tub.

Embodiments of the present disclosure are directed to a nest and tub arrangement for the storage of medical device components. The nest and tub arrangement includes a tub having four side surfaces, and a plurality of guide ribs extending vertically along the side surfaces, wherein the plurality of guide ribs are inwardly directed and include a friction surface extending vertically thereon. The nest and tub arrangement also includes at least one nest having a top surface, a bottom surface, a plurality of receptacles for the storage of a plurality of medical device components therein, and a plurality of deflectable clips positioned on side surfaces of the at least one nest. A position of each of the plurality of deflectable clips of the at least one nest corresponds to a position of a respective one of the plurality of guide ribs of the tub. Furthermore, a portion of each of the plurality of deflectable clips is configured to contact a corresponding friction surface of a respective one of the plurality of guide ribs so as to laterally deflect each of the plurality of deflectable clips inward to align and secure the at least one nest within the tub.

In some embodiments, each of the deflectable clips includes a head portion on a distal end thereof, wherein the head portion is configured to contact the friction surface of a respective one of the plurality of guide ribs when the at least one nest is positioned within the tub.

In some embodiments, a proximal end of each of the deflectable clips is coupled to the at least one nest to enable each of the deflectable clips to deflect inward about the proximal end thereof.

In some embodiments, each of the deflectable clips is positioned within a notched portion of the at least one nest.

In some embodiments, the tub includes a top portion and a bottom portion, the bottom portion being dimensioned smaller than the top portion.

In some embodiments, the top portion is delineated by a bottom ledge surface and a top lid flange, and the plurality of guide ribs extend between the bottom ledge surface and the top lid flange.

In some embodiments, the friction surface of each of the plurality of guide ribs includes an angle of inclination between the bottom ledge surface and the top lid flange, wherein the dimensions at the bottom ledge surface are smaller than the dimensions at the top lid flange.

In some embodiments, the angle of inclination is 1.5° or less.

In some embodiments, the at least one nest further includes at least one finger opening formed therein.

In some embodiments, a flange extending at least partially around each finger opening and extending from the bottom surface of the at least one nest is included.

In some embodiments, the plurality of receptacles include a plurality of frustoconical receptacles sized to hold a plunger stopper therein.

In some embodiments, the at least one nest includes a plurality of nests.

In some embodiments, the plurality of nests are configured to be stackable atop one another within the tub, and a bottommost one of the plurality of nests is configured to be positioned adjacent a bottom ledge surface of the tub.

In some embodiments, the tub includes two long side surfaces and two short side surfaces, wherein each of the two long sides includes two guiding ribs positioned thereon, and wherein each of the two short sides includes one guide rib positioned thereon.

In some embodiments, the at least one nest includes two long sides and two short sides, wherein each of the two long sides includes two deflectable clips, and wherein each of the two short sides includes one deflectable clip.

Further details and advantages of the present disclosure will be understood from the following detailed description read in conjunction with the accompanying drawings.

DESCRIPTION OF THE INVENTION

The following description is provided to enable those skilled in the art to make and use the described aspects contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For the purposes of the description hereinafter, the terms "upper", "lower", "right", "left", "vertical", "horizontal", "top", "bottom", "lateral", "longitudinal", and derivatives thereof shall relate to the invention as it is oriented in the drawings. However, it is to be understood that the invention may assume various alternative variations, except where expressly specified to the contrary. It is also to be understood that the specific devices illustrated in the attached drawings, and described in the following specification, are simply exemplary aspects of the invention. Hence, specific dimensions and other physical characteristics related to the aspects disclosed herein are not to be considered as limiting.

Figure 1:
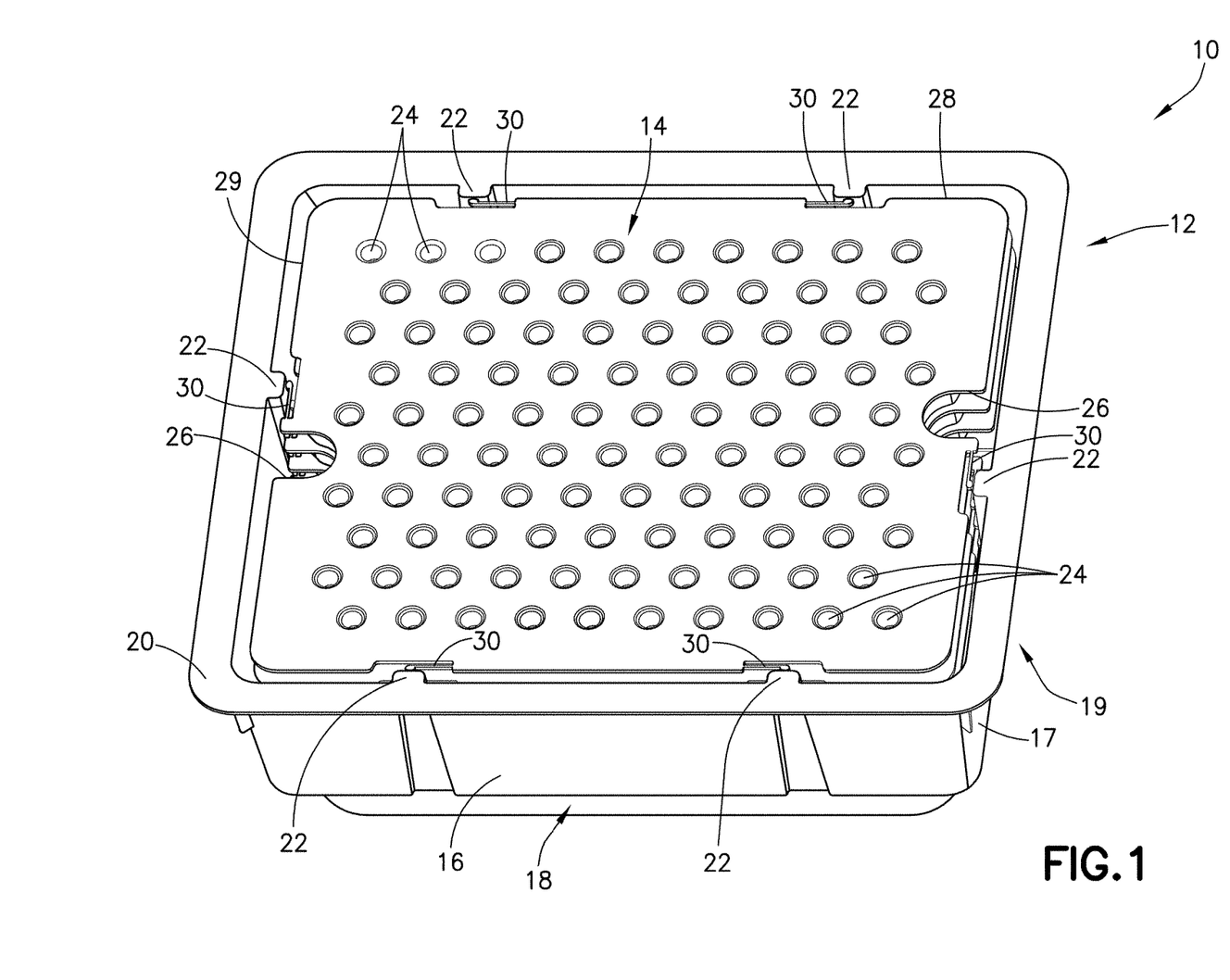
FIG. 1 is a top perspective view of a nest and tub arrangement for the storage of plunger stoppers in accordance with an aspect of the present disclosure.

Referring to FIG. 1, a nest and tub arrangement 10 in accordance with an aspect of the present disclosure is shown. In the nest and tub arrangement 10, a plurality of nests 14 are capable of being removably retained within a tub 12, with each nest 14 configured to hold, e.g., a plurality of plunger stoppers (not shown). For example, the tub 12 may be configured to hold between two and ten nests 14, which the nests stacked vertically relative to one another. As described above, various automated filling machines utilize other nest and tub arrangements in order to store and access medical device components such as, e.g., syringe barrels. Nest and tub arrangement 10, as shown in FIG. 1, is specifically configured to accommodate plunger stoppers in a way that provides for desired positioning and alignment of each nest 14 for accurate handling by the robotic components of the automated filling machines. However, it is to be understood that the present disclosure is not limited to use with plunger stoppers, as the nest and tub arrangements described herein may be utilized with other elements and/or devices.

Figure 2A:
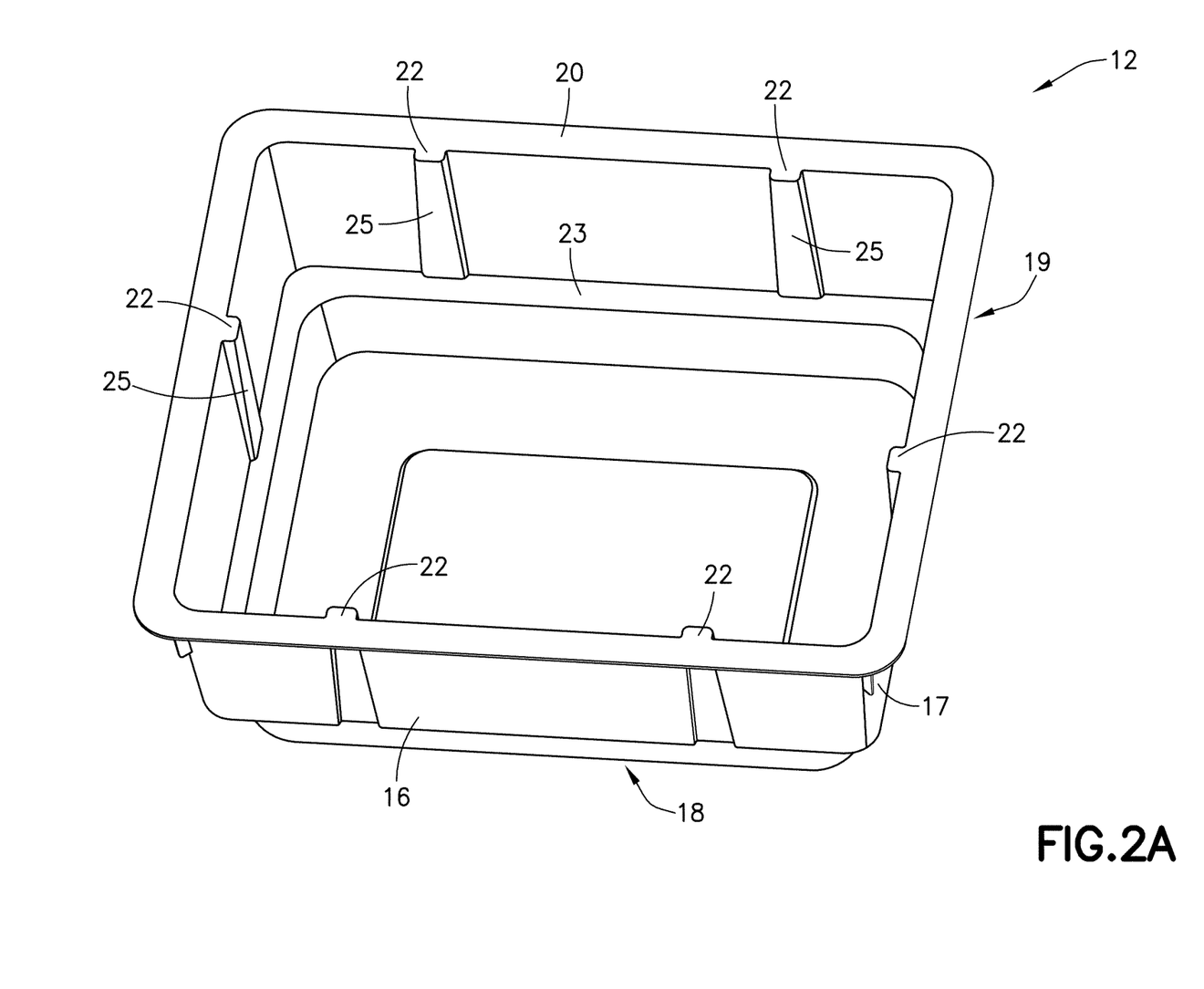
FIG. 2A is a top perspective view of a tub for use in the nest and tub arrangement of FIG. 1.
Figure 2B:
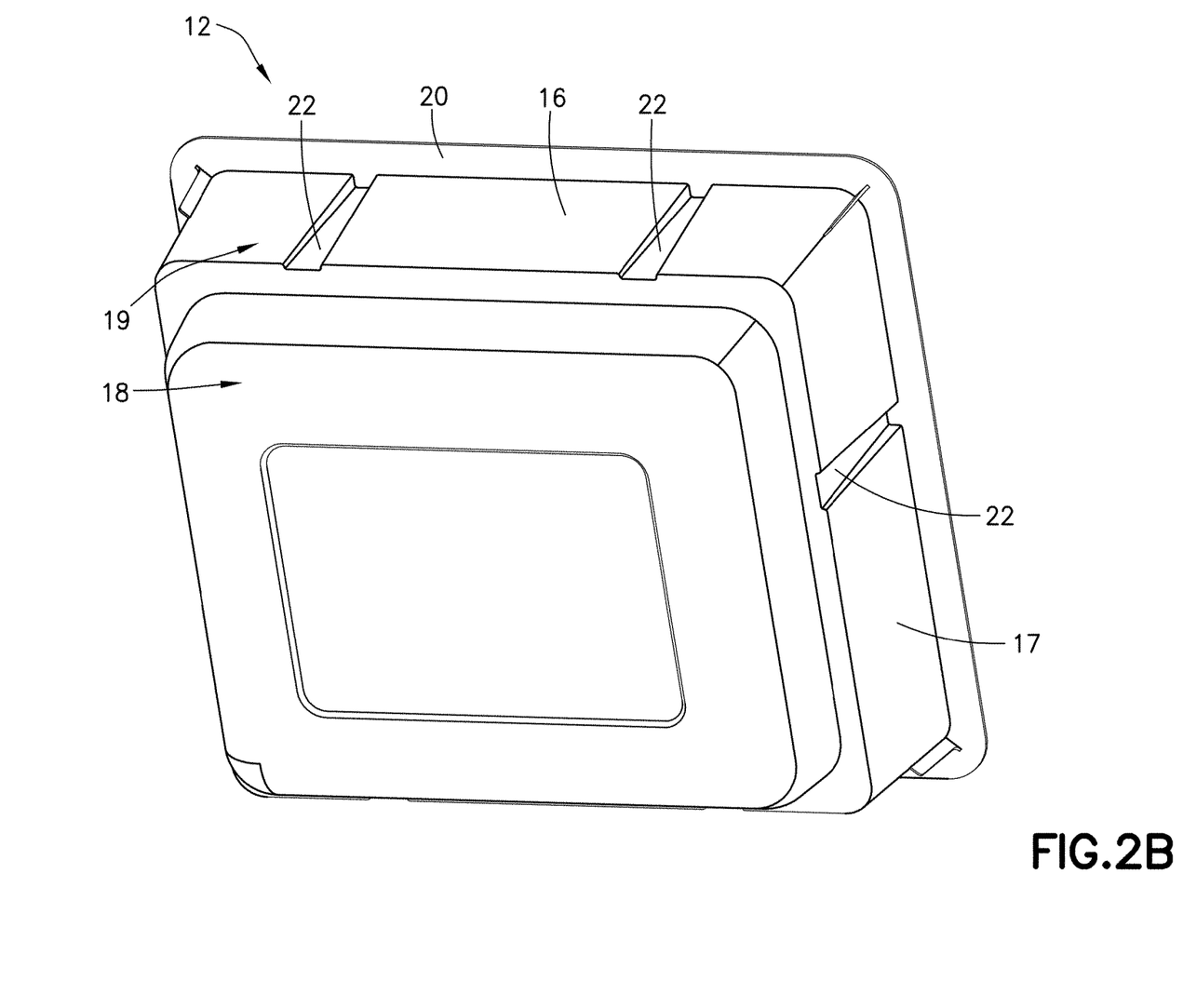
FIG. 2B is a bottom perspective view of the tub of FIG. 2A.

Referring still to FIG. 1, and also to FIGS. 2A and 2B, the tub 12 in accordance with an aspect of the present disclosure is shown. The tub 12 includes a pair of long side surfaces 16 and a pair of short side surfaces 17. However, in alternative embodiments, it is to be understood that the sides of tub 12 need not be different in length and/or parallel, and may instead be, e.g., equal, non-parallel, etc. The general dimensions of the tub 12 (i.e., length, width, and height) may be adapted based on the specific automated filling machine being utilized.

The tub 12 further includes a bottom portion 18 and a top portion 19. Bottom portion 18 is inset from top portion 19, with the bottom portion 18 being dimensioned smaller than the top portion 19, while top portion 19 is delineated by a top lid flange 20 and a bottom ledge surface 23. Such a configuration enables a plurality of tubs 12 to be stacked together during storage, transport, etc., yet allows for sufficient spacing between the respective top lid flanges 20 of stacked tubs 12 so as to enable easy access to (and separation of) tubs 12.

Tub 12 further includes a plurality of guide ribs 22 extending into the interior of the tub along respective side surfaces 16, 17 and between the top lid flange 20 and the bottom ledge surface 23. In the embodiment shown in FIGS. 2A and 2B, the long side surfaces 16 each include two guide ribs 22, while short side surfaces 17 only include one guide rib 22, with each guide rib 22 on the short side surfaces 17 being laterally offset from one another. However, it is to be understood that more or fewer guide ribs 22 may be utilized on the respective side surfaces 16, 17. For example, in alternative embodiments of the present disclosure, the short side surfaces 17 may also include two guide ribs 22, the long side surfaces 16 may include three guide ribs 22, etc.

Each guide rib 22 includes an interior-facing friction surface 25 extending from the top lid flange 20 to the bottom ledge surface 23. As will be described in further detail herein, each friction surface 25 is configured to provide an interface with a corresponding feature on nests 14 in order to reliably align and removably retain the nests 14 within tub 12. In some embodiments, the draft angle of each friction surface 25 of guide ribs 22 (i.e., the angle of inclination of the friction surface 25 between the bottom ledge surface 23 and the top lid flange 20) is relatively small, with the dimensions at the bottom ledge surface 23 being smaller than the dimensions at the top lid flange 20. For example, the draft angle of the friction surface 25 may be less than 1.5°, even if the draft angle of the respective side surfaces 16, 17 is larger than 1.5°. In this way, the nests 14 retained nearer the bottom of the tub 12 may have increased frictional engagement with the friction surface 25 of the guide ribs 22 as compared to those nests 14 positioned nearer the top lid flange 20 of the tub 12. Furthermore, in some embodiments, the nests 14 positioned at or near an upper portion of the tub 12 proximate the top lid flange 20 may not be in contact with the guide ribs 22. Thus, while the nests 14 positioned at or near this upper portion may aid in the alignment of nests 14 nearer a center portion of the tub 12 in the event of movement of tub 12, the nests 14 at or near the upper portion are not necessarily physically retained within the tub 12 via contact with the guide ribs 22.

Tub 12 may be formed of any suitable material, and via any suitable method. For example, tub 12 may be formed of, e.g., a plastic, polymer (e.g., polystyrene), metal, etc., and may be formed by, e.g., molding (e.g., injection molding), thermoforming, stamping, extrusion, welding, etc. Furthermore, tub 12 may be formed as a single piece, or as multiple pieces coupled together. If formed of multiple pieces, the materials forming each piece may be the same or different.

Figure 3A:
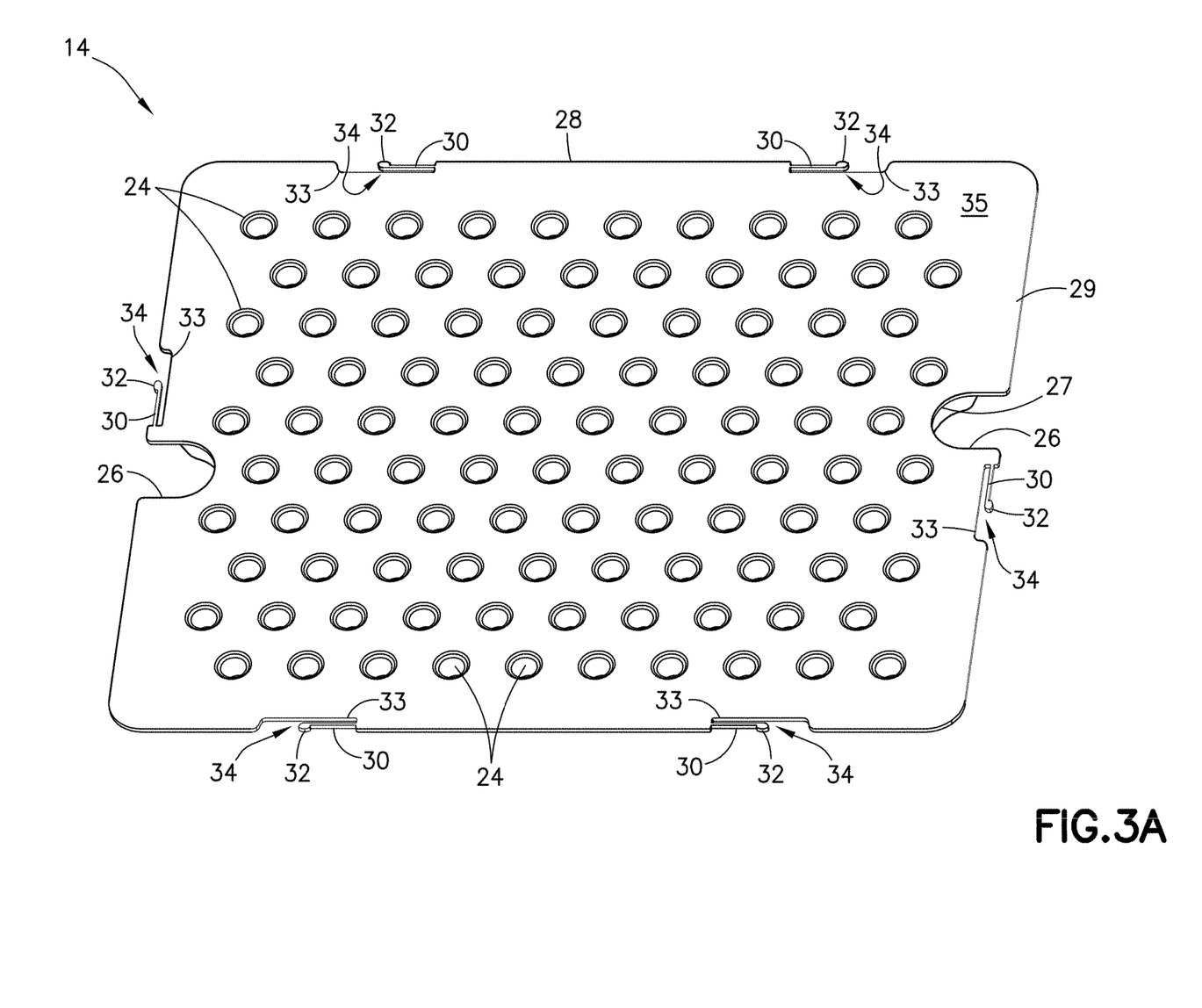
FIG. 3A is a top perspective view of a nest for use in the nest and tub arrangement of FIG. 1.
Figure 3B:
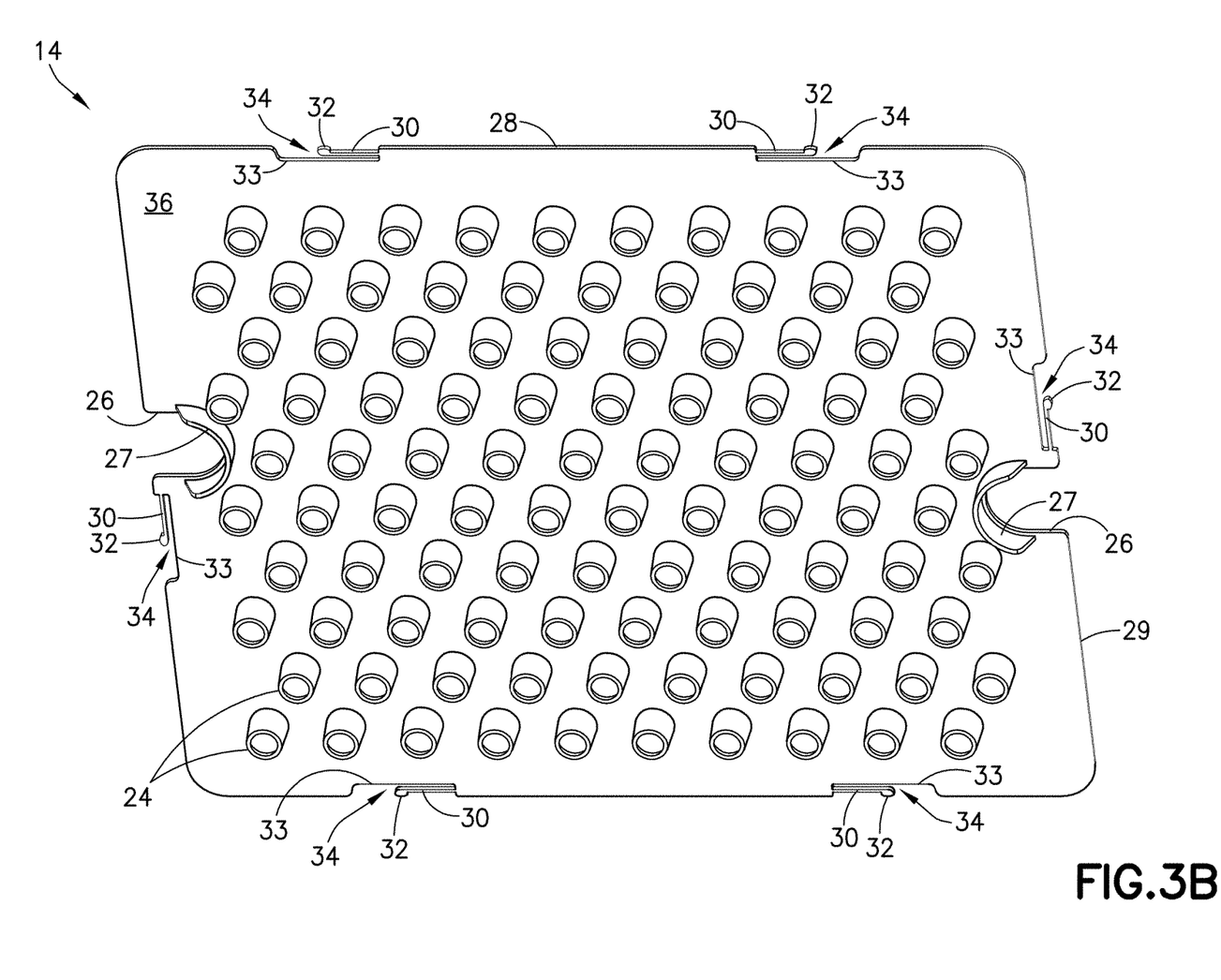
FIG. 3B is a bottom perspective view of the nest of FIG. 3A.

Next, referring to FIGS. 3A and 3B, a nest 14 in accordance with an aspect of the present disclosure is shown. As described above, nest 14 is configured to hold a plurality of plunger stoppers, but it is to be understood that nest 14 may be configured to hold other components.

Specifically, each nest 14 includes a plurality of stopper receptacles 24 formed therein. The stopper receptacles 24 may be formed as substantially frustoconical "chimneys", each capable of holding a plunger stopper therein for access and removal by components of an autonomous filling machine. As shown in FIG. 3A, each stopper receptacle 24 includes an opening formed in a top surface 35 of the nest 14, while the "chimney" of the stopper receptacle 24 extends below a bottom surface 36, as shown in FIG. 3B. The diameter and size of each stopper receptacle 24 may vary based on the type of stopper utilized during a particular filling operation. Thus, it is to be understood that the overall number and positioning of stopper receptacles 24 may also vary as compared to that which is shown in FIGS. 3A and 3B.

Similar to tub 12 described above, each nest 14 includes a pair of long sides 28 and a pair of short sides 29. However, in alternative embodiments, it is to be understood that the sides of nest 14 need not be different in length and/or parallel, and may instead be, e.g., equal, non-parallel, etc. Also like tub 12, the general dimensions of each nest 14 (i.e., length, width, and height) may be adapted based on the specific automated filling machine being utilized.

As shown in FIGS. 3A and 3B, the short sides 29 may each include a finger opening 26 formed thereon, wherein each finger opening 26 is designed to enable simplified manual loading (and/or removal) of the nest 14 into (or from) the tub 12. In some embodiments, a flange 27 may at least partially surround each finger opening 26 and extend from the bottom surface 36 of nest 14, thereby providing the user with a larger surface area upon which to grip the nest 14. While two finger openings 26 are shown on opposing short sides 29 in FIGS. 3A and 3B, it is to be understood that nest 14 may include more or fewer finger openings, either on short sides 29 or long sides 28. Additionally, in some embodiments, the finger openings 26 may be omitted altogether.

Referring still to FIGS. 3A and 3B, nest 14 further includes a plurality of deflectable clips 30. As will be described further herein, the position of each clip 30 on nest 14 coincides substantially with the position of a corresponding guide rib 22 of the tub 12. In this way, the deflectable clips 30 provide a frictional interface between the nest 14 and tub 12, which allows for consistent alignment (and self-centering) of the nest 14 within the tub 12 while still enabling smooth extraction of the nest 14 from the tub 12 during filling operations.

Each clip 30 is formed within a notched portion 33 of the respective sides of nest 14. A proximal end of the clip 30 is coupled to the nest 14, while distal end is free, thereby enabling the clip 30 to deflect inwardly and angularly with respect to the nest 14 about its proximal end. A slot 34 is formed between the clip 30 and the sidewall of the notched portion 33, which allows for inward deflection of the clip 30. At the distal end of clip 30, a head portion 32 is provided, wherein head portion 32 is slightly enlarged as compared to the rest of clip 30. As will be described below, the head portion 32 is configured to provide an interface surface for frictional engagement with the friction surface 25 of each guide rib 22 of tub 12.

In the embodiment shown in FIGS. 3A and 3B, the long sides 28 of the nest 14 include two clips 30, while short sides 29 only include one clip 30, with each clip 30 on the short sides 29 being laterally offset from one another. However, it is to be understood that more or fewer clips 30 may be utilized on the respective sides 28, 29. For example, in alternative embodiments of the present disclosure, the short sides 29 may also include two clips 30, the long sides 28 may include three clips 30, etc. Regardless of the total number of clips 30 provided, it is preferred that the clips 30 of nest 14 correspond in both placement and number to the guide ribs 22 of tub 12 so as to ensure proper alignment.

Each nest 14 may be formed of any suitable material, and via any suitable method. For example, nest 14 may be formed of, e.g., a plastic, polymer (e.g., polystyrene), metal, etc., and may be formed by, e.g., molding (e.g., injection molding), thermoforming, stamping, extrusion, welding, etc. Furthermore, nest 14 may be formed as a single piece, or as multiple pieces coupled together. If formed of multiple pieces, the materials forming each piece may be the same or different.

Figure 4:
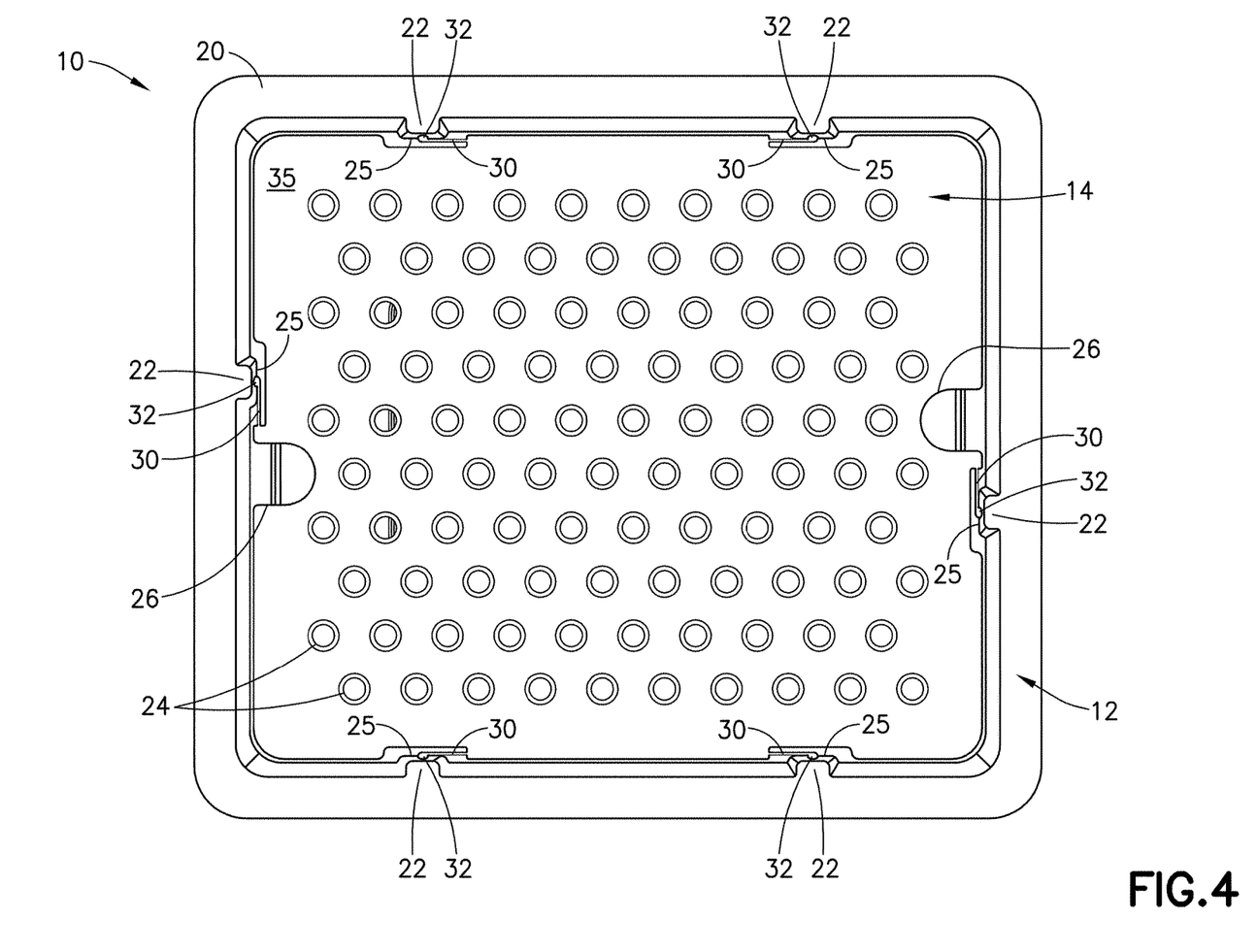
FIG. 4 is a top plan view of the nest and tub arrangement of FIG. 1.

Referring to FIG. 4, a nest 14 is shown positioned within tub 12 in accordance with an aspect of the present disclosure. As noted above, the head portion 32 of each clip 30 is configured to contact the friction surface 25 of a corresponding guide rib 22, providing a plurality of frictional interfaces between the nest 14 and the tub 12. As the nest 14 is pressed into the tub 12, the clips 30 are each configured to deflect inwardly, thereby maintaining a deflection force between the head portion 32 and the friction surface 25 which acts to both center and retain the nest 14 within the tub 12. The deflection force of the clips 30 is high enough to maintain the nest 14 in an aligned, centered position, but not so high as to increase the friction force between the head portion 32 and the fiction surface 25 to a level which inhibits smooth removal of the nest 14 from the tub 12. For example, in one embodiment, the global deflection force of all clips 30 may be a maximum of about 2.6 N, equating to a maximum of about 0.4 N per clip when six clips are utilized on the nest 14. However, it is to be understood that the nest and tub arrangement in accordance with various aspects of the present disclosure are not limited as such, and the global deflection force (and deflection force per clip) may be smaller or larger than the example provided above.

As was also noted above, a plurality of nests 14 may be stored within tub 12, with the nests stacked atop one another between the bottom ledge portion 23 and the top lip portion 20 of the tub 12. While the friction surfaces 25 may have a slight draft angle (e.g., 1° or less), the configuration of the clips 30 compensates for the natural undercut of the guide ribs 22, enabling each nest 14 to be centered and secured within the top portion 19 of tub 12 regardless of its position within the stack. That is, the clips 30 of the bottommost nest 14 in a stack of nests may deflect inwardly a greater amount than the clips 30 of the uppermost nest 14 due to the draft angle of the guiding ribs 22. For example, the clips 30 of the bottommost nest 14 may deflect about 1 mm, and the clips 30 of the uppermost nest 14 may deflect only about 0.5 mm, with the clips 30 of the nests 14 positioned therebetween deflecting between those amounts. Such a variation in deflection enables the nests 14 to remain aligned and secured within the tub 12, regardless of their stack position.

Figure 5:
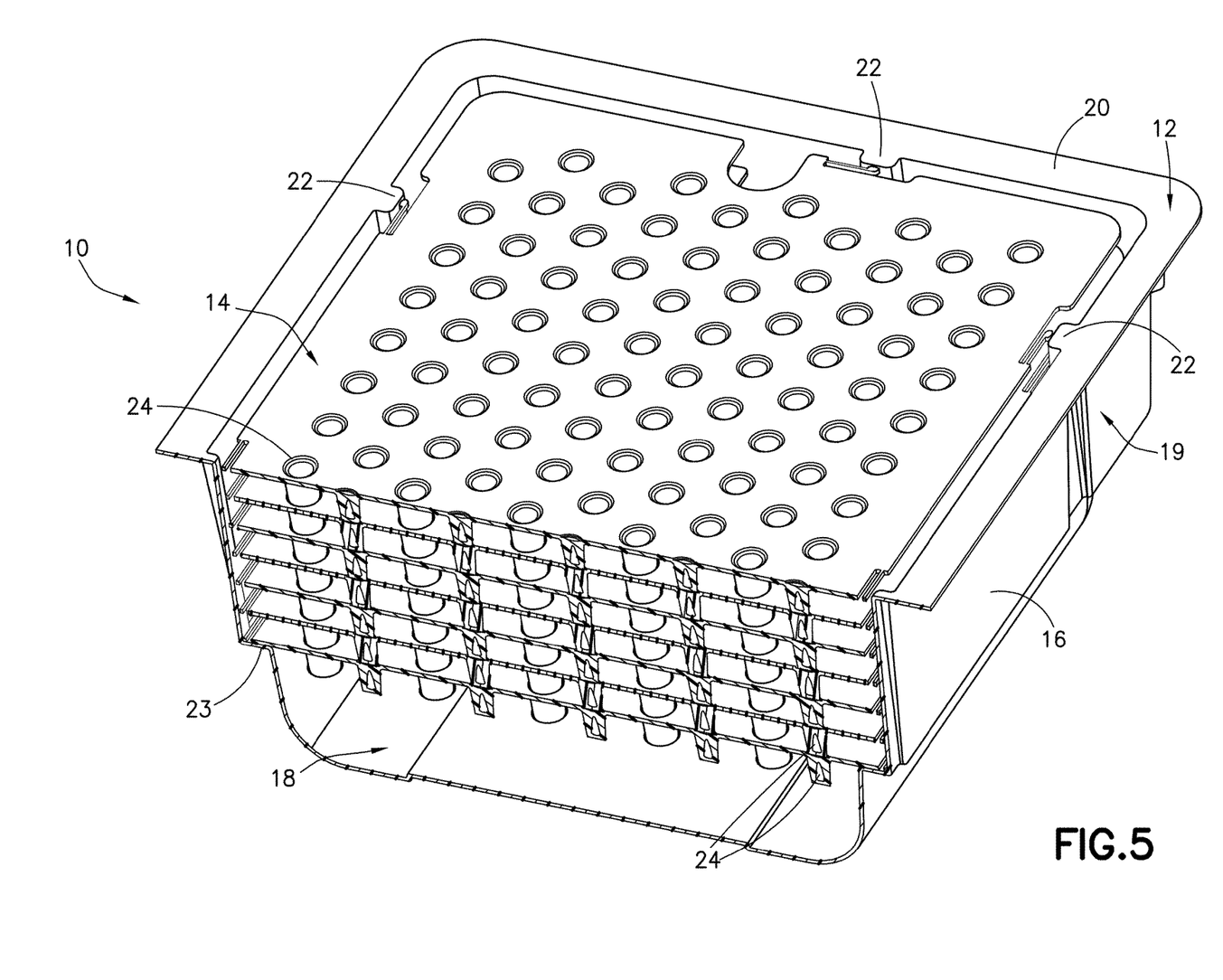
FIG. 5 is a cross-sectional perspective view of the nest and tub arrangement of FIG. 1.

Referring now to FIG. 5, a cross-sectional view of the nest and tub arrangement 10 in accordance with an aspect of the present disclosure is shown. In the embodiment shown in FIG. 5, seven nests 14 are shown stacked within tub 12. The bottommost nest 14 is positioned adjacent the bottom ledge surface 23 of tub 12, and may at least partially rest on the bottom ledge surface 23, while the uppermost nest 14 is positioned slightly below the top lid flange 20, and each stopper receptacle 24 is vertically aligned with the stopper receptacle 24 above and below (if applicable). While the embodiment in FIG. 5 illustrates seven nests 14, it is to be understood that more or fewer nests may be held within the tub in other embodiments.

With the nest and tub arrangement 10 shown and described with respect to FIGS. 1-5, a plurality of plunger stoppers may be held in a plurality of nests 14, with each nest 14 being removably retained within a tub 12. In this way, the nest and tub arrangement 10 may be utilized by various automated filling machines that necessitate precise alignment, minimal "play" of both components and their storage means, and ready access to syringe components, including plunger stoppers.

While several embodiments of a nest and tub arrangement are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A nest and tub arrangement for the storage of medical device components, comprising:
    a tub comprising:
        four side surfaces, and
        a plurality of guide ribs extending vertically along the side surfaces, wherein the plurality of guide ribs are inwardly directed and include a friction surface extending vertically thereon; and
    at least one nest comprising:
        a top surface,
        a bottom surface,
        a plurality of receptacles for the storage of a plurality of medical device components therein, and
        a plurality of deflectable clips positioned on side surfaces of the at least one nest,
    characterized in that
        a position of each of the plurality of deflectable clips of the at least one nest corresponds to a position of a respective one of the plurality of guide ribs of the tub, and
        a portion of each of the plurality of deflectable clips is configured to contact a corresponding friction surface of a respective one of the plurality of guide ribs so as to laterally deflect each of the plurality of deflectable clips inward to align and secure the at least one nest within the tub.

2. The nest and tub arrangement according to claim 1, wherein each of the deflectable clips comprises a head portion on a distal end thereof, and wherein the head portion is configured to contact the friction surface of a respective one of the plurality of guide ribs when the at least one nest is positioned within the tub.

3. The nest and tub arrangement according to claim 1, wherein a proximal end of each of the deflectable clips is coupled to the at least one nest to enable each of the deflectable clips to deflect inward about the proximal end thereof.

4. The nest and tub arrangement according to claim 1, wherein each of the deflectable clips is positioned within a notched portion of the at least one nest.

5. The nest and tub arrangement according to claim 1, wherein the tub comprises a top portion and a bottom portion, the bottom portion being dimensioned smaller than the top portion.

6. The nest and tub arrangement according to claim 5, wherein the top portion is delineated by a bottom ledge surface and a top lid flange, and wherein the plurality of guide ribs extend between the bottom ledge surface and the top lid flange.

7. The nest and tub arrangement according to claim 6, wherein the friction surface of each of the plurality of guide ribs comprises an angle of inclination between the bottom ledge surface and the top lid flange, wherein the dimensions at the bottom ledge surface are smaller than the dimensions at the top lid flange.

8. The nest and tub arrangement according to claim 7, wherein the angle of inclination is 1.5° or less.

9. The nest and tub arrangement according to claim 1, wherein the at least one nest further comprises at least one finger opening formed therein.

10. The nest and tub arrangement according to claim 9, further comprising a flange extending at least partially around each finger opening and extending from the bottom surface of the at least one nest.

11. The nest and tub arrangement according to claim 1, wherein the plurality of receptacles comprise a plurality of frustoconical receptacles sized to hold a plunger stopper therein.

12. The nest and tub arrangement according to claim 1, wherein the at least one nest comprises a plurality of nests.

13. The nest and tub arrangement according to claim 12, wherein the plurality of nests are configured to be stackable atop one another within the tub, and further wherein a bottommost one of the plurality of nests is configured to be positioned adjacent a bottom ledge surface of the tub.

14. The nest and tub arrangement according to claim 1, wherein the tub comprises two long side surfaces and two short side surfaces, wherein each of the two long sides comprises two guiding ribs positioned thereon, and wherein each of the two short sides comprises one guide rib positioned thereon.

15. The nest and tub arrangement according to claim 14, wherein the at least one nest comprises two long sides and two short sides, wherein each of the two long sides comprises two deflectable clips, and wherein each of the two short sides comprises one deflectable clip.

* * * * *